United States Patent [19]

Skalen

[11] Patent Number: 4,860,576

[45] Date of Patent: Aug. 29, 1989

[54] DEVICE IN VISCOSITY METERS

[75] Inventor: Bengt Skalen, Saffle, Sweden

[73] Assignee: BTG Kalle Inventing AB, Sweden

[21] Appl. No.: 240,152

[22] Filed: Sep. 2, 1988

[30] Foreign Application Priority Data

Sep. 4, 1987 [SE] Sweden ................................ 8703445

[51] Int. Cl.⁴ .......................................... G01N 11/14
[52] U.S. Cl. ...................................................... 73/59
[58] Field of Search ....................................... 73/59, 60

[56] References Cited

U.S. PATENT DOCUMENTS

| | | | |
|---|---|---|---|
| 2,305,531 | 12/1942 | Hurndall | 73/60 |
| 3,269,171 | 8/1966 | Bruss et al. | 73/60 |
| 4,214,475 | 7/1980 | Carter et al. | 73/59 |
| 4,299,118 | 11/1981 | Gau et al. | 73/60 X |
| 4,485,450 | 11/1984 | Characklis et al. | 73/60 X |
| 4,524,611 | 6/1985 | Richon et al. | 73/59 |

Primary Examiner—Stewart J. Levy
Assistant Examiner—Joseph W. Roskos
Attorney, Agent, or Firm—Ostrolenk, Faber, Gerb & Soffen

[57] ABSTRACT

The invention relates to a device in viscosity meters for measuring the viscosity of liquid having a large number of contaminants and a low viscosity, the meter including an inner cylinder (5) rotatably mounted in a stationary, outer cylinder (1) in a liquid projecting from a drive unit (12), there being a gap (4) forming a measuring zone between the cylinders (1,5) liquid being propelled through the gap with the aid of a propeller (3) arranged in front of the inner cylinder (5) and in a cavity (10) in the outer cylinder (1). The inner cylinder (5) is provided with an edge (6) projecting out into the gap (4) and the outer cylinder (1) has at least one slot (7) extending in its longitudinal direction and in the flow direction of the liquid, for enabling discharge of the contaminants fastening between the edge (6) and the outer cylinder (1), a self-cleaning strainer system thus being achieved, where the particles in the liquid only negligibly disturb measurement.

4 Claims, 1 Drawing Sheet

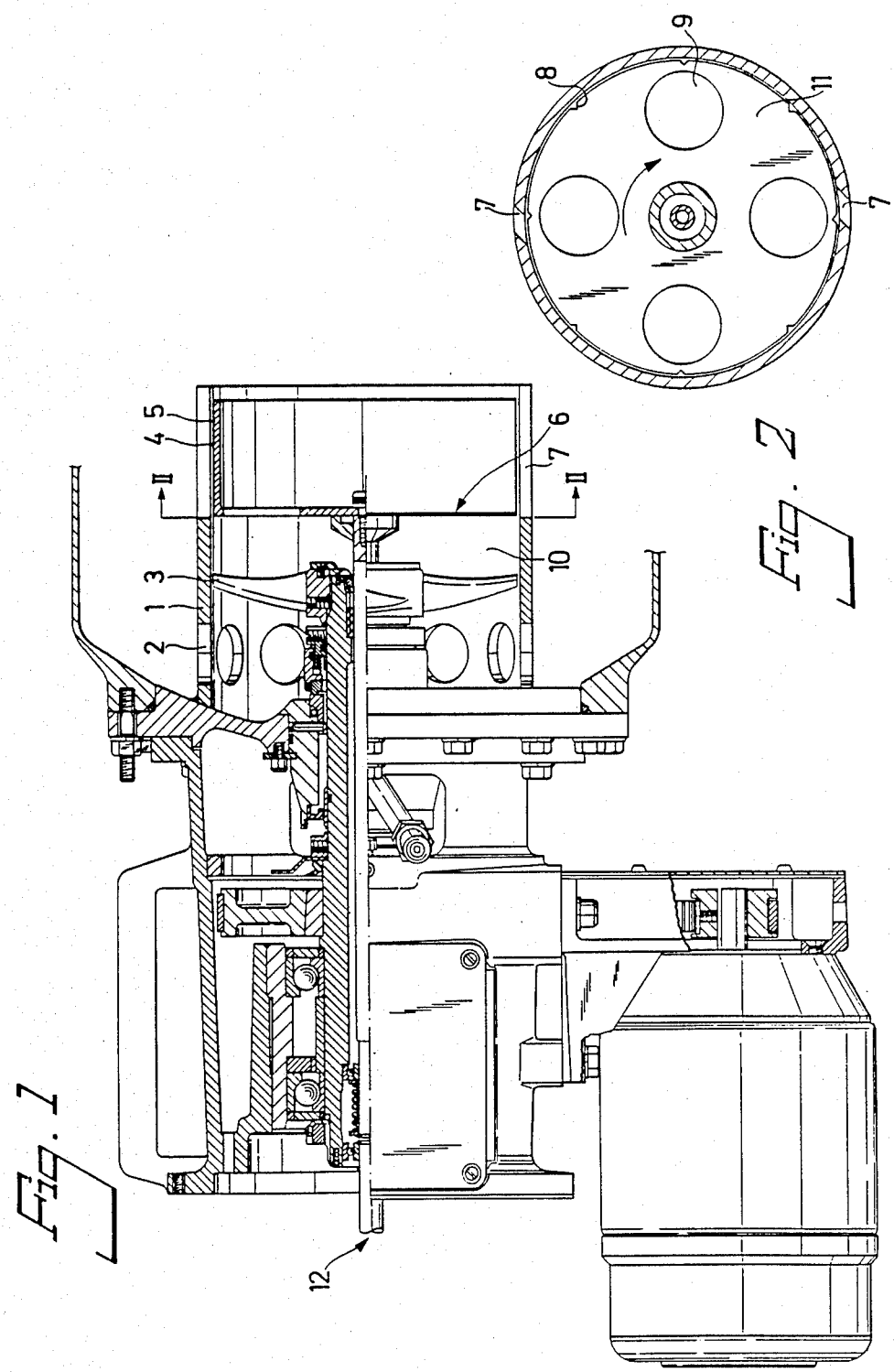

DEVICE IN VISCOSITY METERS

SUMMARY OF THE INVENTION

The present invention relates to a meter for measuring viscosity in liquids with a great number of contaminants and with low viscosity, the meter including an inner cylinder rotatably mounted in a stationary, outer cylinder in a liquid and, projecting from a drive unit, a gap forming a measuring zone between the cylinders, liquid being propelled through the gap with the aid of a propeller arranged in front of the inner cylinder and in a cavity in the outer cylinder.

The object of the invention is to provide an apparatus for use in viscosity meters of the type mentioned above, intended for measuring viscosity in liquids with viscosities down to 20 cp (1 cp centipoise), and as examples of the liquids envisaged, which can be measured with the meter, can be mentioned black liquor, coal sludge, and liquids in the foodstuffs industry.

The meter, in accordance with the present invention, has a built-in self-cleaning strainer system where particles in the medium only negligibly disturb the measurement. The measurement takes place between a stationary and rotating cylinder and a measuring torque then occurs which is linear to the viscosity of the medium.

The distinguishing features of the device in accordance with the present invention are disclosed in the following claims.

The invention will now be described below in more detail and with reference to the accompanying drawing.

BRIEF DESCRIPTION OF THE DRAWINGS

FIG. 1 is a schematic cross section of the viscosity meter in accordance with the preferred embodiment of the invention, and FIG. 2 is a section along the line II—II in FIG. 1.

DESCRIPTION OF THE PREFERRED EMBODIMENTS

As will be seen in FIGS. 1 and 2, the viscosity meter in accordance with the invention includes a stationary outer cylinder 1, which projects out from a drive unit 12 intended for driving a propeller 3 and a rotatably mounted inner cylinder 5, both of which are situated inside the outer cylinder 1, with the inner cylinder 5 downstream of the propeller 3, seen in the direction of liquid flow. There are a plurality of holes 2 in the cylindrical surface of the outer cylinder 1 for propelling liquid with the aid of the propeller 3 into a cavity 10 in the outer cylinder 1. Between cylinders 1 and 5 there is a gap 4, forming a measuring zone, and through this gap the liquid which is to be measured is propelled with the aid of the propeller 3. The outer cylinder 1 has at least one slot 7 extending in its longitudinal direction and in the direction of the liquid flow, this slot having the task of discharging contaminants which may come between an edge 6 and the outer cylinder 1, whereby the straining property of the device is further improved.

For preventing splinters and the like from lying against the outer cylinder 1 without moving, so that they can be conveyed out through the slots 7 in the outer cylinder 1, the edge 6 of the inner cylinder 5 is provided with a plurality of indentations 8 uniformly distributed around its periphery, enabling splinters and other particles which fasten against the outer cylinder 1 to rotate around with the inner cylinder 5 and come out through the slots 7. Larger particles which come into the cavity 10 of the outer cylinder 1 pass out through holes 9 in the end wall 11 of the rotatably mounted inner cylinder 5. These holes 9 must therefore be larger than the holes 2 in the outer cylinder 1.

The device in accordance with the present invention functions in the following manner. Liquid, or the medium in question, is sucked into the outer cylinder 1 via the holes 2 in its cylindrical surface with the aid of the propeller 3 and further into the measuring zone between the stationary outer cylinder 1 and the rotating inner cylinder 5. To prevent contaminants from coming into the measuring zone in the gap 4 and disturbing the measurement, the inner cylinder is provided with the edge 6, which has the function of limiting the length of the disturbance, whereby a particle which comes between the edge 6 and the outer cylinder 1 only disturbs measurement during the time it takes for the particle to pass the edge 6.

What is claimed is:

1. A self-cleaning and straining meter for measuring the viscosity of liquids which have a large number of contaminants and a low viscosity, said meter comprising:
   an outer cylinder, said outer cylinder defining a cavity therein;
   an inner cylinder rotatably mounted within said outer cylinder;
   a drive unit connected to said inner cylinder for rotating said inner cylinder within said outer cylinder;
   a gap located between said cylinders, said gap forming a measuring chamber; and
   a propeller for propelling liquid through said gap, said propeller being located upstream from said inner cylinder and within said cavity;
   wherein said inner cylinder has an edge which projects into said gap and wherein said outer cylinder has a longitudinally extending slot through which contaminants fastened between said edge and said outer cylinder are discharged as said inner cylinder rotates so that the contaminants only negligibly disturb the measurement of viscosity.

2. The meter as claimed in claim 1, wherein said edge has a periphery and wherein a plurality of indentations are uniformly distributed around said periphery.

3. The meter as claimed in claim 1, wherein said inner cylinder has an end wall with at least two holes for discharging large particles.

4. The meter as claimed in claim 3, wherein said outer cylinder has a plurality of holes for permitting liquid to enter said cavity, said holes of said outer cylinder being smaller than said holes of said end wall.

* * * * *